United States Patent [19]

Miyama et al.

[11] Patent Number: 4,733,130
[45] Date of Patent: Mar. 22, 1988

[54] INSULATING TUBE SURROUDING ANODE TUBE IN ANALYTICAL GLOW DISCHARGE TUBE

[75] Inventors: Takao Miyama; Tanaka Shoichi; Fukui Isao, all of Kyoto, Japan

[73] Assignee: Shimadzu Corporation, Kyoto, Japan

[21] Appl. No.: 799,375

[22] PCT Filed: Feb. 26, 1985

[86] PCT No.: PCT/JP85/00086
§ 371 Date: Oct. 24, 1985
§ 102(e) Date: Oct. 24, 1985

[87] PCT Pub. No.: WO85/04015
PCT Pub. Date: Sep. 12, 1985

[51] Int. Cl.$^4$ ............ H01J 1/88; H01J 17/04
[52] U.S. Cl. ................... 313/619; 313/620; 313/146
[58] Field of Search ............ 313/618, 619, 620, 146, 313/148; 356/313, 316

[56] References Cited

U.S. PATENT DOCUMENTS 3,543,077 11/1970 Grimm ........................... 313/210
3,909,652 9/1975 Ferre et al. ..................... 313/146

Primary Examiner—David K. Moore
Assistant Examiner—K. Wieder
Attorney, Agent, or Firm—Armstrong, Nikaido, Marmelstein & Kubovcik

[57] ABSTRACT

A glow discharge tube for exciting a sample in emission spectrochemical analysis or mass spectrometry, in which glow discharge is effected between the anode tube and the sample while gas is being passed, for exhaust, through the narrow gap formed between the sample surface and the end of the insulating tube fit on the anode tube so as to maintain a constant pressure in the anode tube. Since the insulating tube projects further than the anode tube toward the sample side, a shortcircuit is never formed between the anode and the cathode even if sample vapor adheres to the walls surrounding the exhaust passage. As a result, efficient analysis can be achieved with the glow discharge tube of the present invention.

4 Claims, 3 Drawing Figures

INSULATING TUBE SURROUDING ANODE TUBE IN ANALYTICAL GLOW DISCHARGE TUBE

FIELD OF THE INVENTION

The present invention relates to an apparatus for analyzing components in samples using glow discharge, more particularly to an improved glow discharge tube in the apparatus.

BACKGROUND OF THE INVENTION

Conventionally, glow discharge is utilized as exciting source in analyzing components in samples. When glow discharge is effected between an anode and a sample set on the cathode side, cathode sputtering occurs so that the surface of the sample is dispersed in the discharge region where it is excited for emission. The light thus emitted is taken out for spectrochemical analysis to analyze the components. The glow discharge tube used in the above conventional emission spectrochemical analysis is well known through the disclosure in Japanese Patent Registration No. 760451 (Patent Publication No. SHO49-21680).

The conventional glow discharge tube is schematically shown in FIG. 3. A hollow anode body "A" has a window "W" at the front through which light is taken out. An anode tube "T" extends from the anode body "A" into the cavity in a cathode body "K", and a sample "S" is set so that it closes the opening of the cavity in the cathode body "K". An insulating plate "I" is inserted between the cathode body "K" and the anode body "A" for electrical insulation. Discharge gas such as argon is introduced from an intake port "In" and exhausted from and exhaust port 01 formed in the anode body and an exhaust port 02 formed in the cathode body "K". Thus the glow discharge region is formed in the space in the anode tube "T". The sample constituents dispersed by cathode sputtering and suspended in form of vapor in the discharge region is excited for emission.

Thus, in the conventional glow discharge tube with the anode tube "T" inserted in the cavity in the cathode body "K" and with a gap G4 left between the anode tube "T" and the cathode body "K", the sample is set in such a manner as to close one open end of the cavity so that a glow discharge region is formed between the anode tube "T" and the sample whose potential is maintained at the same level as that of the cathode body "K". With the glow discharge tube of such a construction, however, the discharge gap G3 between the sample and the anode tube end must be set at the specified width while maintaining an appropriate vacuum (2~20 Torr) in the discharge region, in order to secure proper glow discharge. To this purpose, discharge gas is forcedly exhausted through the port formed in the circumferential wall of the anode tube during glow discharge in said discharge region.

The sample vapor suspended in the discharge region flows with the exhaust gas stream and sticks to the surrounding walls of the gaps G3 and G4. As a result, the gaps G3 and G4 tend to be bridged, shortcircuiting the anode tube "T" with the sample "S" as well as with the cathode body "K". To prevent such a trouble, the user is often required to dismount the sample "S" and the cathode body "K" from the anode body "A" to clean the surrounding walls of the gaps G3 and G4. If the sample is a zinc-plated steel sheet which produces a large quantity of sputtering, cleaning is required after almost every analysis. In reassembling the discharge tube after cleaning, great care must be taken so that the anode tube "T" does not touch the cathode body "K". Though the analysis itself takes 1~3 minutes, the entire operation for analysis requires more than five times as long as that, because the cleaning operation takes about 15 minutes. This is a serious problem when continuous analysis is needed as in the quality control in the production of plated steel sheets. In addition, reproducibility of the analysis with the conventional glow discharge tube is impaired, because the dimensions of the gaps G3 and G4 can change every time the glow discharge tube is disassembled and reassembled. To ensure proper glow discharge without shortcircuiting, the gap G3 between the sample "S" and the anode tube end should be desirably 0.3~0.5 mm, which may be somewhat varied according to the sample material, applied voltage and purpose of the analysis. In view of the suitable pressure required for the discharge region (2~20 Torr of vacuum is required.), however, it is desirable to make the gap G3 as narrow as possible to effect larger resistance against exhaust gas flow.

In the conventional discharge tube, the dimension of the gap G3 is limited by the discharge gap requirement. The exhaust passage G4 surrounding the anode tube is, therefore, made long and narrow, to increase the exhaust resistance for the discharge region, thereby maintaining the required vacuum. This is why a shortcircuit is caused by the sticking sample vapor as described earlier.

BRIEF SUMMARY OF THE INVENTION

It is the object of the present invention to provide an improved glow discharge tube which eliminates the above mentioned problems of the conventional glow discharge tube. According to the present invention, an insultating tube is fit on an anode tube, an end of the insulating tube projecting beyond the anode tube toward the sample side so that a gap narrower than a discharge gap is formed as an exhaust passage between the insulating tube and the sample surface. The thus formed exhaust passage provides a resistance against exhaust gas flow. Glow discharge takes place between the sample and the anode tube end which retreats back from the insulating tube end. Even if the gap is bridged by sample vapor adhering to the walls on both sides of the gap as the vapor is flowing with the exhaust gas stream, therefore, shortcircuit will never occur.

DESCRIPTION OF THE PREFERRED EMBODIMENT

Figure 1:
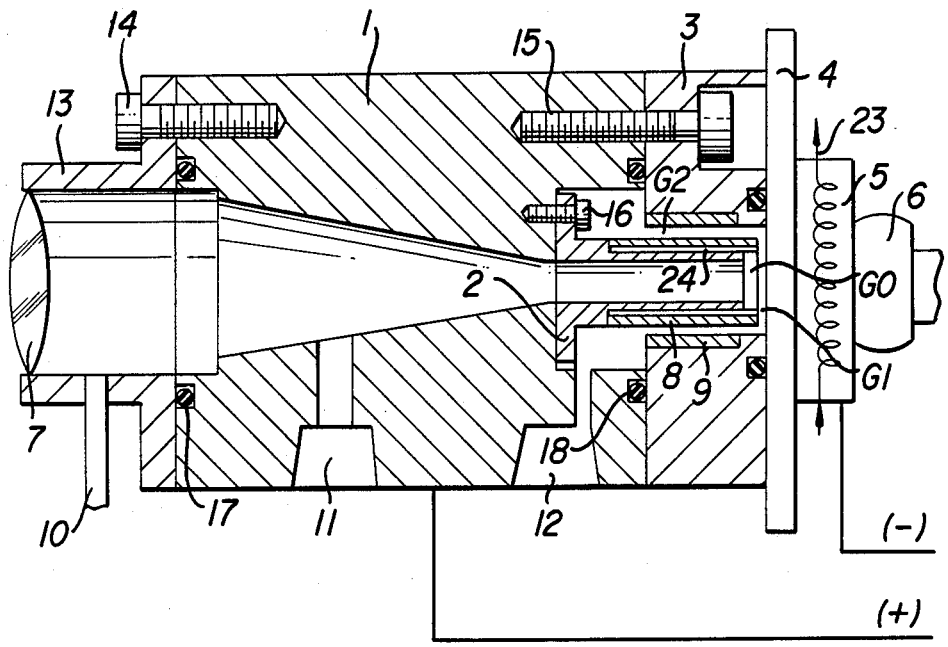
FIG. 1 is a sectional view of a glow discharge tube for emission spectrochemical analysis as an example of the present invention.

The present invention will be described in detail, with reference to the accompanying drawings. FIG. 1 shows an example of a glow discharge tube for emission spectrochemical analysis according to the present invention. In FIG. 1, an anode tube 2 connected to an anode body 1 is surrounded by an insulating tube 8, the end of the insulating tube 8 projecting beyond the anode tube 2 toward a sample 4. The sample 4 is pressed against a mantle 3 by a conductive sample supporting block 5 and a resilient sample holder 6, so as to face the end of the anode tube. The mantle 3 is an insulating member and has a conductor 9 fit on the side facing a gap G2 (exhaust passage). Numeral 7 denotes a condenser leading the excitation light to a spectroscope. 13 is a supporting member of the condenser 7. 14, 15 and 16 are clamp bolts and 17, 18 and 19 are seal rings to shut off the external air. Positive voltage is applied through the anode body 1 to the anode tube 2, while negative voltage is applied through the sample supporting block 5 to the sample 4 which may be a plated steel sheet or a steel sheet on which an analysis object such as a semiconductor is stuck. Discharge gas (argon) is introduced through an intake port 10 and exhausted through exhaust ports 11 and 12 to a vacuum pump.

As described earlier, in the conventional glow discharge tube, the exhaust resistance for the discharge region is determined by the discharge gap set between the sample surface and the anode tube end. One of the features of the present invention is, in contrast, that the exhaust resistance for the discharge region is set independent of the discharge gap. Specifically, the gap between the anode tube 2 and the sample may only define a discharge gap, while resistance against the exhaust gas flow is determined by the gap between the insulating tube 8 and the sample. Therefore, the gap between the sample 4 and the anode tube 2 can be set to 0.3~0.5 mm depending upon the analysis object and purpose, so as to prevent a shortcircuit from occurring due to the sample vapor adhesion. Meanwhile, the gap G1 between the sample 4 and the end of the insulating tube 8 is set narrower than the discharge gap G0, that is, about 0.2 mm. According to this example, the insulating tube 8 is 2 mm in the wall thickness, which is large enough for the gap G1 to effect an exhaust resistance to maintain a suitable pressure in the discharge region. In FIG. 1, the insulating tube 8 is connected to the anode tube 2 through thread so that it is axially movable slightly with respect to the anode tube 2. 24 is the threaded joint portion.

Thus, according to the example shown in FIG. 1, cathode sputtering uniformly takes place at the circular portion on the sample 4 facing the end of the anode tube 2, with an optimal pressure for glow discharge being maintained in the anode tube 2. Sample vapor generated by the cathode sputtering passes through the gaps G1 and G2 and is exhausted. As passing through the gaps, the sample vapor can adhere to and bridge the walls surrounding the gaps G1 and G2, but never cause a shortcircuit between the anode and the cathode, giving no influence on the measurement. Besides, the bridge is formed only partially in the gaps, and therefore does not hamper the exhaust gas flow. Thus, analysis can be kept on without interruption. The anode body 1, the mantle 3 and the sample supporting block 5 are equipped with embedded water flow passages 23 so that they are cooled. Only a part of the water flow passages 23 is shown in FIG. 1. The insulating tube need not always have the outer circumferential configuration as shown in FIG. 1, provided that it fits on the anode tube.

If the entire walls surrounding the gap G2 (exhaust passage) were made of insulating material, unstable fluctuation would occur in the voltage between the cathode and the anode, possibly resulting in the poor analysis accuracy. That is, if ions adhere to the insulating surfaces that define the gap G2, uneven potential distribution would result due to localized electric charge, thus causing discharge which would give influence on the voltage between the cathode and the anode. For this reason, the conductor 9 is set on the mantle 3 in the example shown in FIG. 1. The conductor 9 effects even potential distribution so that voltage fluctuation described above is prevented. The conductor 9 is not directly connected to the anode nor the cathode.

Figure 2:
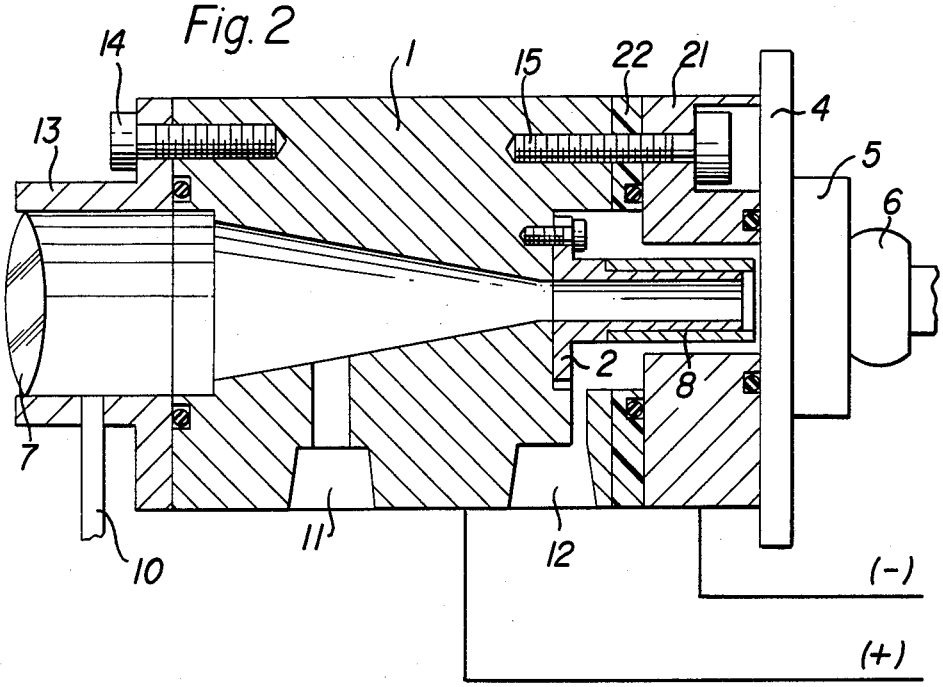
FIG. 2 is a sectional view of a glow discharge tube as another example of the invention.
Figure 3:
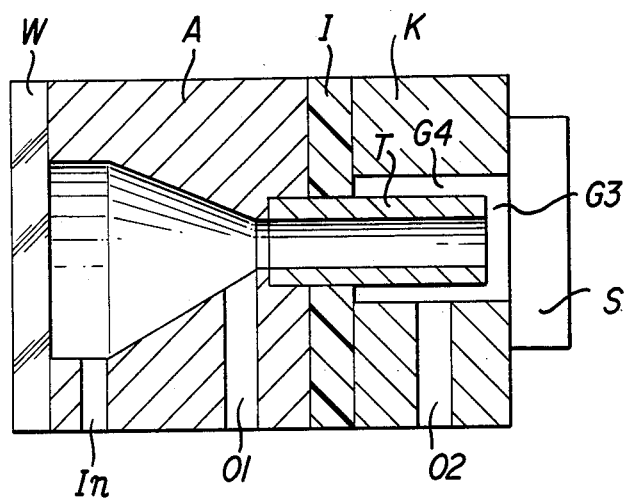
FIG. 3 is a schematical view showing the conventional glow discharge tube for emission spectrochemical analysis.

Another example of the present invention is shown in FIG. 2 which illustrates a glow discharge tube for emission spectrochemical analysis. In FIG. 2, the same parts as those in FIG. 1 are allotted with the same reference numbers. The example in FIG. 2 is different from that in FIG. 1 in the point that the mantle 21 against which the sample 4 is pressed is made of conductive material and connected through an insulating plate 22 to the anode body 1 by the insulating clamp screw 15. The mantle 21 and the sample 4 constitute a cathode, with negative voltage being supplied through the mantle 21 to the sample 4. Negative voltage may be supplied to the sample 4 through the sample supporting block 5 instead of the mantle 21. The example shown in FIG. 2 has the same advantageous effect as the example shown in FIG. 1.

In either of the examples in FIGS. 1 and 2, no electrical shortcircuit takes place, even if the gap G2 (exhaust passage) is bridged due to sample vapor adhesion. Accordingly, once the glow discharge tube has been assembled, it can be used for a long period (almost forever), without necessity of disassembling for cleaning the walls surrounding the exhaust passage G2. Similarly, no electric shortcircuit takes place in the gap G1 if bridged. Only consideration required in adjusting the gap G1 is, therefore, to achieve the pressure most suitable for glow discharge in the anode tube.

In the example in FIG. 1, since the insulating tube 8 is connected through thread with the anode tube 2, the gap G1 is variable. The present invention is also advantageous in the point that, if the sample is depressed by the air pressure toward the anode tube, the insulating tube 8 prevents the sample from touching the anode tube so that no electrical shortcircuit is formed. A thin sample can be set for analysis, therefore, without no consideration of electrical shortcircuit. The practical utility of the glow discharge tube is therefore significantly improved in the present invention.

In the above examples, the invention is utilized for emission spectrochemical analysis. Not only to the emission spectrochemical analysis, the present invention is also applicable to other analyzes such as mass spectrometry. If the invention is used for mass spectrometry, the anode body and the anode tube are made shorter, and the generated ions of the sample are taken out to be led to the mass spectrometer that uses the electromagnetic field.

POTENTIAL APPLICABILITY IN INDUSTRY

As indicated in the above description, the glow discharge tube of the present invention is a useful exciting source for a sample in the emission spectrochemical analysis, mass spectrometry, etc, and is applicable to analyzers to identify the components of various substances such as plated steel sheets and semiconductor wafers.

What is claimed is:

1. An analytical glow discharge tube in which a sample as a cathode is placed facing an anode tube end with a specified discharge gap therebetween, and wherein gas in the discharge gap is directed to the outer side of the anode tube so as to be exhausted, said discharge tube comprising:

an insulating tube disposed around said anode tube and spaced apart from said sample, an end of said insulating tube projecting beyond said anode tube end toward said sample such that said gas is exhausted around the outer circumferences of said insulating tube, and wherein an exhaust passage, for said exhaust gas flowing in the discharge region between the anode and the cathode, has a width narrower than said discharge gap.

2. The analytical glow discharge tube as claimed in claim 1, wherein said glow discharge tube has a mantle, said exhaust passage being formed between the mantle and the outer circumferential surface of the insulating tube as well as to help the sample to be set in an appropriate position to achieve the discharge gap.

3. The analytical glow discharge tube as claimed in claim 2, wherein the mantle is an insulating member having a conductor set on the wall surrounding said exhaust passage, the conductor being connected to neither of the anode and the cathode.

4. The analytical glow discharge tube as claimed in claim 1, wherein said insulating tube disposed around said anode tube is axially movable with respect to said anode tube.

* * * * *